US010591425B2

(12) United States Patent
Sato et al.

(10) Patent No.: US 10,591,425 B2
(45) Date of Patent: Mar. 17, 2020

(54) X-RAY DIFFRACTION MEASUREMENT METHOD AND APPARATUS

(71) Applicant: HONDA MOTOR CO., LTD., Minato-ku, Tokyo (JP)

(72) Inventors: Kenji Sato, Wako (JP); Kazuhito Nakao, Wako (JP)

(73) Assignee: HONDA MOTOR CO., LTD., Tokyo (JP)

(*) Notice: Subject to any disclaimer, the term of this patent is extended or adjusted under 35 U.S.C. 154(b) by 268 days.

(21) Appl. No.: 15/872,064

(22) Filed: Jan. 16, 2018

(65) Prior Publication Data

US 2018/0202948 A1 Jul. 19, 2018

(30) Foreign Application Priority Data

Jan. 19, 2017 (JP) ................. 2017-007155

(51) Int. Cl.
*G01N 23/207* (2018.01)
*G01N 23/20* (2018.01)

(52) U.S. Cl.
CPC ..... *G01N 23/207* (2013.01); *G01N 2223/0566* (2013.01); *G01N 2223/316* (2013.01); *G01N 2223/32* (2013.01); *G01N 2223/323* (2013.01)

(58) Field of Classification Search
CPC ..... G01N 2223/323; G01N 2223/0566; G01N 2223/316; G01N 23/207; G01N 223/0568
See application file for complete search history.

(56) References Cited

U.S. PATENT DOCUMENTS 10,436,723 B2 * 10/2019 Osakabe ........... G21K 1/06
2013/0129052 A1 5/2013 Toraya et al.

FOREIGN PATENT DOCUMENTS

| JP | 2000-275113 | 10/2000 |
| JP | 2015-132527 | 7/2015 |
| WO | 2012015053 | 2/2012 |

* cited by examiner

*Primary Examiner* — Don K Wong
(74) *Attorney, Agent, or Firm* — Amin, Turocy & Watson, LLP (57) ABSTRACT

An X-ray diffraction measurement method includes an arranging step of arranging a shielding plate and a two-dimensional detector on an outgoing optical axis, and a calculating step of calculating a diffraction profile indicating an X-ray intensity with respect to a diffraction angle of the object to be measured, on the basis of a two-dimensional X-ray image detected by the two-dimensional detector. In the arranging step, the shielding plate is arranged in a manner so that the slit is inclined at least in a direction about the outgoing optical axis with respect to an orthogonal direction which is orthogonal to both the incident optical axis and the outgoing optical axis.

7 Claims, 8 Drawing Sheets

X-RAY DIFFRACTION MEASUREMENT METHOD AND APPARATUS

CROSS-REFERENCE TO RELATED APPLICATION

This application is based upon and claims the benefit of priority from Japanese Patent Application No. 2017-007155 filed on Jan. 19, 2017, the contents of which are incorporated herein by reference.

BACKGROUND OF THE INVENTION

Field of the Invention

The present invention relates to an X-ray diffraction measurement method and apparatus for measuring properties of an object to be measured by detecting an X-ray diffraction pattern of X-rays produced by the object to be measured.

Description of the Related Art

Conventionally, an X-ray diffraction measurement method has been known for measuring properties of an object to be measured by detecting a diffraction pattern (hereinafter also simply referred to as a "pattern") by irradiating X-rays toward the object to be measured. For example, in order to improve measurement efficiency, various methods have been proposed in which a combination of a two-dimensional slit and a two-dimensional detector is used.

In Japanese Laid-Open Patent Publication No. 2015-132527, an X-ray diffraction measurement apparatus has been proposed, which is equipped with a slit plate in which a curved slit is formed in a shielding plate. By rotating the slit plate around a reference axis, it is possible to scan through diffraction angles while the arrangement of the two-dimensional detector remains fixed.

SUMMARY OF THE INVENTION

However, with the apparatus proposed in Japanese Laid-Open Patent Publication No. 2015-132527, since a rotation mechanism for rotating the slit plate is required, the size of the apparatus is large in scale, which results in an increase in manufacturing costs.

The present invention has been devised taking into consideration the aforementioned problems, and has the object of providing an X-ray diffraction measurement method and apparatus, which are capable of effectively measuring an object to be measured by a one-time X-ray detection operation.

An X-ray diffraction measurement method according to a first aspect of the present invention is a method for measuring properties of an object to be measured by detecting an X-ray diffraction pattern produced by the object to be measured at an intersecting position where an incident optical axis and an outgoing optical axis intersect one another, comprising an arranging step of arranging on the outgoing optical axis a shielding plate having a linear slit formed therein, and a two-dimensional detector which is capable of detecting within a detection region X-rays that have passed through the slit, and a calculating step of calculating a diffraction profile indicating an X-ray intensity with respect to a diffraction angle of the object to be measured, on the basis of a two-dimensional X-ray image detected by the two-dimensional detector, wherein, in the arranging step, the shielding plate is arranged in a manner so that the slit is inclined at least in a direction about the outgoing optical axis with respect to an orthogonal direction which is orthogonal to both the incident optical axis and the outgoing optical axis.

In the forgoing manner, by inclining the slit at least in a direction about the axis of the outgoing direction with respect to the orthogonal direction which is orthogonal to both the incident optical axis and the outgoing optical axis, the passage of X-rays is limited in a manner so as to ensure uniqueness of the mapping. Stated otherwise, the diffraction position and the diffraction angle are uniquely determined from the two-dimensional position lying within the detection region, and a diffraction profile corresponding to the diffraction position can be calculated on the basis of the detected two-dimensional X-ray image. Consequently, the object to be measured can effectively be measured by a one-time X-ray detection operation.

Further, in the calculating step, one or a plurality of diffraction profiles corresponding to diffraction positions of the object to be measured may be calculated using geometric information in relation to the intersecting position, the slit, and the detection region. Since the slit is a linear slit, diffraction profiles corresponding to respective diffraction positions can be calculated using a comparatively simple geometric calculation.

Further, the object to be measured may be a polycrystalline object including a material with orientational disorder and having a thickness greater than or equal to 10 μm, and the object to be measured may be arranged at an orientation so that the thickness direction of the object lies parallel to the incident optical axis. In accordance with this feature, properties at each of respective positions in the thickness direction can be measured simultaneously by a one-time X-ray detection operation.

Further, the object to be measured may be an object in which layered bodies including a polycrystalline material with orientational disorder are stacked, and the object to be measured may be arranged at an orientation so that a stacking direction of the layered bodies lies parallel to the incident optical axis. In accordance with this feature, properties at each of the respective layered bodies can be measured simultaneously by a one-time X-ray detection operation.

Further, the two-dimensional detector may be a photon counting type of detector, and in the calculating step, in a state in which the object to be measured, the shielding plate, and the two-dimensional detector are fixed, a time series of diffraction profiles may be calculated on the basis of two-dimensional X-ray images detected sequentially by the two-dimensional detector. In accordance with this feature, properties of the object to be measured can be measured in time series, and a so-called dynamic analysis can be performed.

Further, the shielding plate may be disposed so as to be capable of rotating with respect to the outgoing optical axis. In accordance with this feature, it is possible to change the direction of inclination of the slit to an orientation that is suitable for making measurements in accordance with the type of object to be measured.

An X-ray diffraction measurement apparatus according to a second aspect of the present invention is an apparatus adapted to measure properties of an object to be measured by detecting an X-ray diffraction pattern produced by the object to be measured at an intersecting position where an incident optical axis and an outgoing optical axis intersect one another, comprising a shielding plate having a linear slit formed therein, a two-dimensional detector which is capable of detecting within a detection region X-rays that have passed through the slit, and a profile calculating unit adapted to calculate a diffraction profile indicating an X-ray intensity with respect to a diffraction angle of the object to be measured, on the basis of a two-dimensional X-ray image detected by the two-dimensional detector, wherein the shielding plate and the two-dimensional detector are disposed respectively on the outgoing optical axis, and the shielding plate is arranged in a manner so that the slit is inclined at least in a direction about the outgoing optical axis with respect to an orthogonal direction which is orthogonal to both the incident optical axis and the outgoing optical axis.

In accordance with the X-ray diffraction measurement method and apparatus according to the present invention, the object to be measured can effectively be measured by a one-time X-ray detection operation.

The above and other objects, features, and advantages of the present invention will become more apparent from the following description when taken in conjunction with the accompanying drawings, in which a preferred embodiment of the present invention is shown by way of illustrative example.

DESCRIPTION OF THE PREFERRED EMBODIMENTS

A preferred embodiment of an X-ray diffraction measurement method according to the present invention in relation to an X-ray diffraction measurement apparatus will be presented and described below with reference to the accompanying drawings.

[Configuration of X-Ray Diffraction Measurement Apparatus 10]

Figure 1:
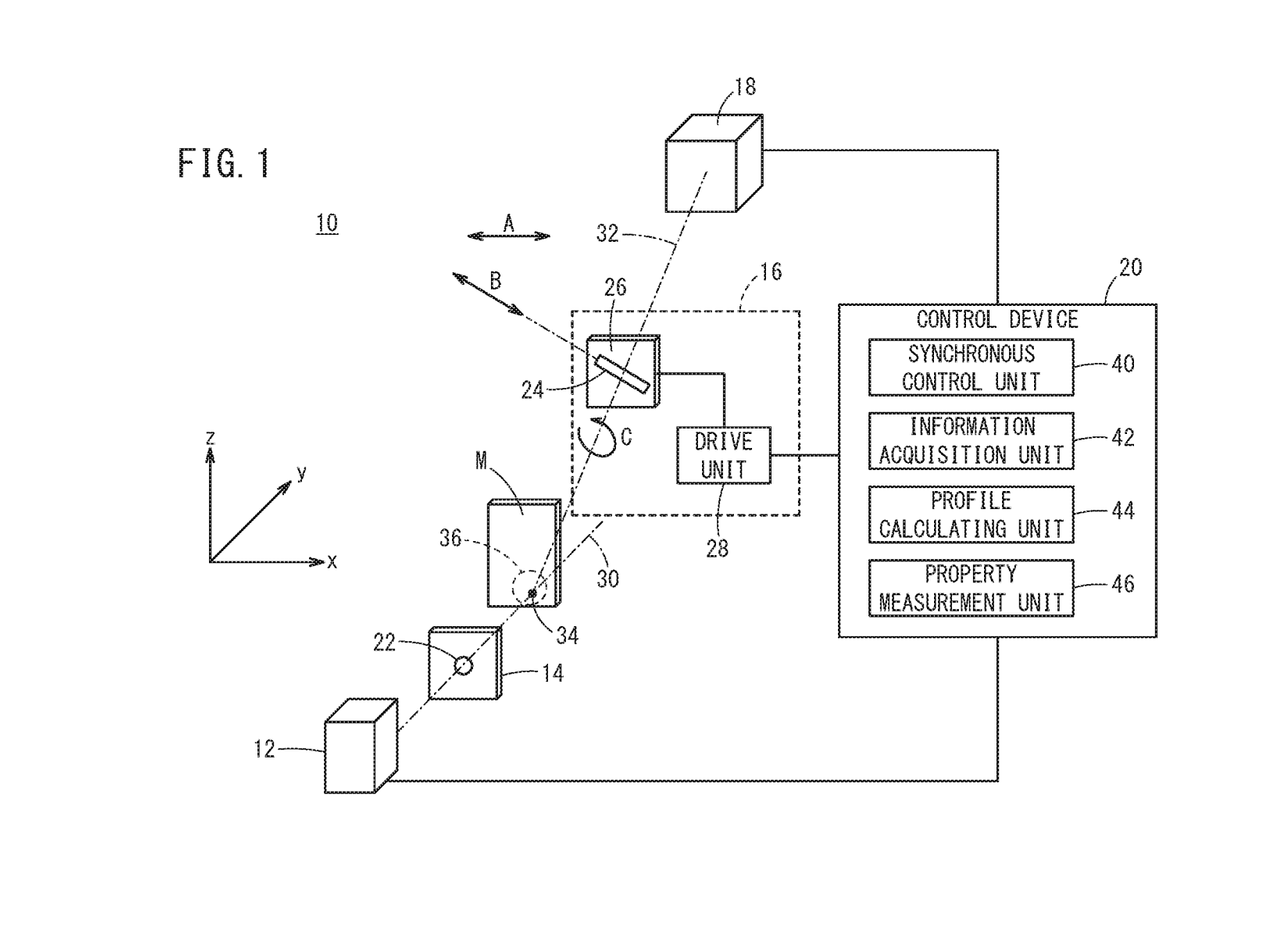
FIG. 1 is a configuration diagram of an X-ray diffraction measurement apparatus according to an embodiment of the present invention.

FIG. 1 is a configuration diagram of an X-ray diffraction measurement apparatus 10 according to an embodiment of the present invention. The X-ray diffraction measurement apparatus 10 is an apparatus adapted to measure properties of an object to be measured M, by detecting an X-ray diffraction pattern of X-rays produced by the object to be measured M. According to the present embodiment, an apparatus configuration is shown in which a transmission type of X-ray diffraction method is performed. However, an apparatus configuration may also be adopted which is applicable to a reflection type of X-ray diffraction method.

The X-ray diffraction measurement apparatus 10 is constituted to include an X-ray generator 12, an incident side shielding mechanism 14, an outgoing side shielding mechanism 16, a two-dimensional detector 18, and a control device 20.

The X-ray generator 12 is equipped with a thermoelectron type, a field emission type, or a Schottky type of electron gun, and radiates X-rays toward the exterior. Alternatively, the X-ray generator 12 may be an insertion light source (more specifically, an undulator or a wiggler) which is disposed in various types of accelerators including a synchrotron, a storage ring, a linac, and a microtron.

The incident-side shielding mechanism 14 is a shielding mechanism for limiting the passage of X-rays from the X-ray generator 12, and is constituted from an X-ray shielding plate, an X-ray reflecting mirror, an X-ray collimator, an X-ray conduit, or a combination thereof. In the example shown in the drawing, the incident side shielding mechanism 14 is a pinhole shielding plate having a pinhole 22 therein.

The outgoing side shielding mechanism 16 is a shielding mechanism adapted to limit the passage of X-rays that are diffracted by the object to be measured M. The outgoing side shielding mechanism 16 comprises a shielding plate 26 having a linear slit 24 formed therein, and a drive unit 28 which is capable of driving the shielding plate 26. More specifically, the drive unit 28 rotates the shielding plate 26 about a predetermined axis in accordance with a control signal from the control device 20.

The two-dimensional detector 18 is a device that acquires a two-dimensional X-ray image 70 (FIG. 6A) by detecting X-rays that have passed through the slit 24, and may be either one of an integrating type detector or a photon counting type detector. Examples of a photon counting type detector include a scintillation detector, a solid state detector (SSD), an avalanche photodiode (APD), and a PILATUS (Pixel Apparatus for the SLS).

Incidentally, a representative light beam, which is formed by connecting the X-ray generator 12, the pinhole 22, and the object to be measured M by a single straight line, is referred to as an "incident optical axis 30". Also, a representative light beam, which is formed by connecting the object to be measured M, the slit 24, and the two-dimensional detector 18 by a single straight line, is referred to as an "outgoing optical axis 32". The outgoing optical axis 32 intersects the incident optical axis 30 at one intersecting position 34. Stated otherwise, by arranging the object to be measured M at the intersecting position 34, diffraction (i.e., a diffraction pattern) of X-rays at a site (hereinafter referred to as a measurement site 36) including the intersecting position 34 and positions in the vicinity thereof is detected.

The xyz coordinate system shown in the drawing is an orthogonal coordinate system, in which the direction of the incident optical axis 30 is defined as a "y-axis", and in which a plane including the incident optical axis 30 and the outgoing optical axis 32 is defined as a "yz plane". In this case, both the incident optical axis 30 and the outgoing optical axis 32 are orthogonal to the "x-axis" (hereinafter also referred to as an "orthogonal direction A"). In this instance, it should be noted that the shielding plate 26 is arranged in a manner so that the slit 24 is inclined with respect to the orthogonal direction A. Hereinafter, the longitudinal direction of the slit 24 may also be referred to as a "direction of inclination B".

In the illustrated example, the two-dimensional detector 18 and the shielding plate 26 are arranged with a positional relationship in which an X-ray detection surface and the formation surface of the slit 24 are parallel to each other. More specifically, the shielding plate 26 is capable of being rotated in a direction C about the outgoing optical axis 32 while the aforementioned parallel relationship is maintained.

The control device 20 is configured to include a CPU (Central Processing Unit) and a memory, and serves as a computer that controls respective components of the X-ray diffraction measurement apparatus 10 (for example, the X-ray generator 12, the two-dimensional detector 18, and the drive unit 28). By reading out and executing programs stored in the memory, the control device 20 functions as a synchronous control unit 40, an information acquisition unit 42, a profile calculating unit 44, and a property measurement unit 46.

[Measurement Problems]

Figure 2:
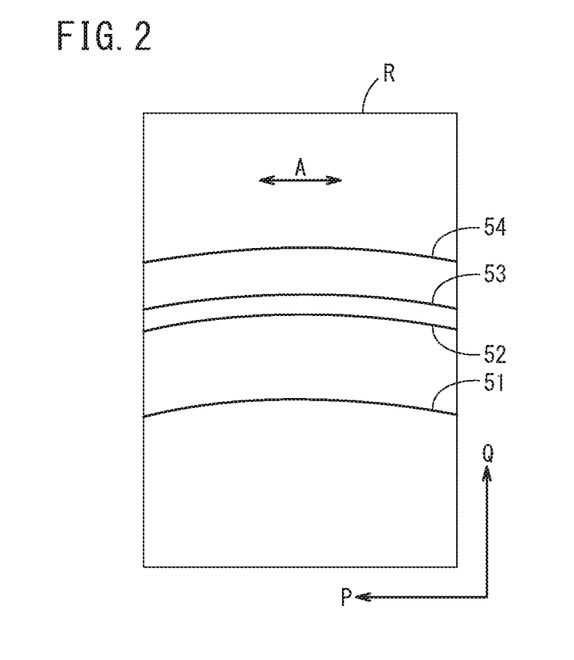
FIG. 2 is a diagram showing an X-ray diffraction image of a positive electrode plate of a single layer cell.

FIG. 2 is a diagram showing an X-ray diffraction image of a positive electrode plate of a single layer cell. The diagram schematically illustrates detection results in the case that X-rays are irradiated onto the object to be measured M under a condition in which the shielding plate 26 (see FIG. 1) is provisionally removed. Hereinafter, for facilitating the description, it is assumed that optical blurring occurs to the same extent in the two-dimensional detector 18, regardless of the presence or absence of the shielding plate 26.

The rectangular region corresponds to a detection region R on the two-dimensional detector 18 (see FIG. 1). In the detection region R, positions where the detected X-ray intensity is small are indicated in white, and positions where the detected X-ray intensity is large are indicated in black. Further, in the detection region R, the short side direction thereof is defined as a P-axis, and the long side direction thereof is defined as a Q-axis, respectively. It should be noted that the P-axis direction coincides with the aforementioned orthogonal direction A.

The positive electrode active material is composed of a material having four peaks at diffraction angles lying close to each other (roughly, 25 degrees <2θ<30 degrees). In this case, partial images of Debye-Scherrer rings (hereinafter referred to as "Debye rings") are simultaneously and distinguishably detected as arcuate patterns 51 to 54 extending along the orthogonal direction A within the detection region R.

As can be understood from the positional relationship shown in FIG. 1, the pattern 51 having a smaller diffraction angle has a smaller Q coordinate within the detection region R. Conversely, as the diffraction angle of the pattern 54 becomes larger, the Q coordinate increases within the detection region R.

Figure 3A:
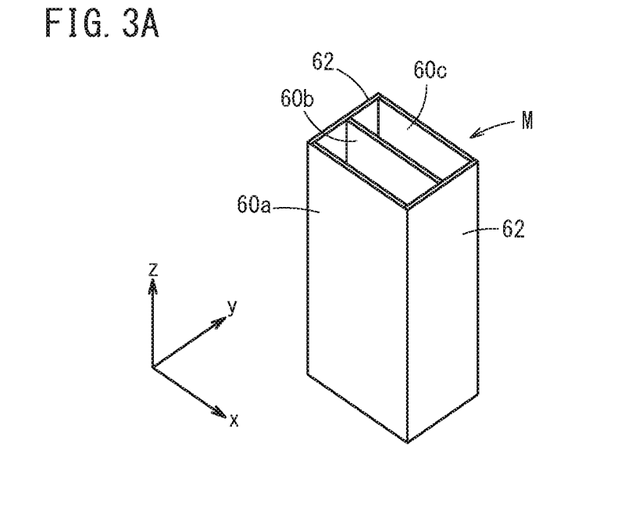
FIG. 3A is a perspective view of an object to be measured in which the structure of a lithium ion battery is simulated.

FIG. 3A is a perspective view of the object to be measured M in which the structure of a lithium ion battery is simulated. The object to be measured M is composed of three layered bodies 60a, 60b, 60c corresponding to the positive electrode plate described in FIG. 2, and two fixed plates 62, 62 for fixing the layered bodies 60a to 60c from both sides thereof.

Figure 3B:
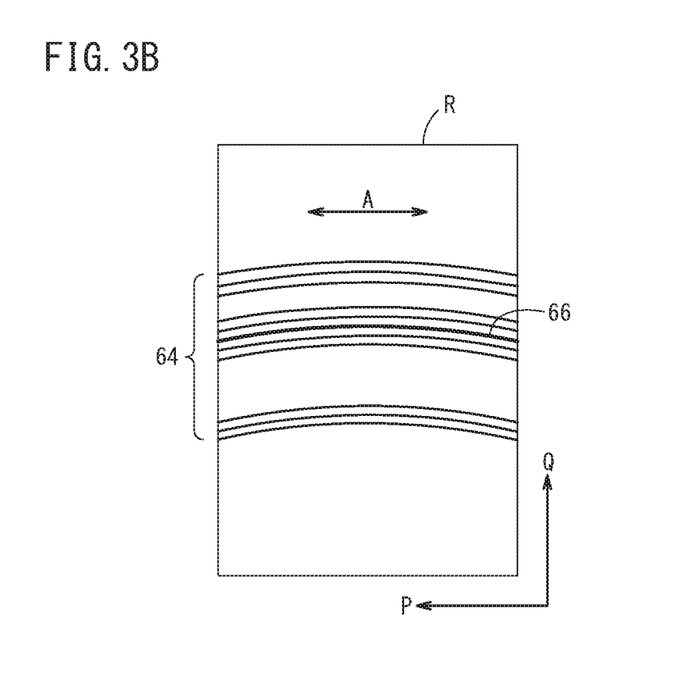
FIG. 3B is a diagram showing an X-ray diffraction image taken with the object to be measured shown in FIG. 3A.

FIG. 3B is a diagram showing an X-ray diffraction image taken with the object to be measured M shown in FIG. 3A. Similar to the case of FIG. 2, this diagram schematically illustrates detection results in the case that X-rays are irradiated onto the object to be measured M under a condition in which the shielding plate 26 (see FIG. 1) is removed.

As can be understood from the diagram, within the detection region R, the patterns 51 to 54 (see FIG. 2) in the layered bodies 60a to 60c are detected simultaneously as a linear pattern group 64 in which the patterns 51 to 54 are translated in parallel along the Q-axis direction and overlap one another. However, the pattern 53 in the layered body 60a on the frontmost side, and the pattern 52 in the layered body 60c on the rearmost side are overlapped with each other and detected as such. Stated otherwise, when the overlapping portion 66 indicated by the thick line is regarded as one pattern, the linear pattern group 64 consists substantially of eleven patterns.

In this manner, phenomenologically speaking, in the case that portions of the plurality of patterns 51 to 54 are overlapped in accordance with the shape or the arrangement of the object to be measured M, a problem results in that it becomes difficult to separate and discriminate the individual patterns 51 to 54 from each other. Such a phenomenological problem will be described below from a geometrical perspective.

In the case that X-rays are irradiated onto the object to be measured M, the diffracted X-rays reach a two-dimensional position within the detection region R which is determined geometrically, corresponding to a combination of the diffraction position on the object to be measured M and the diffraction angle. Stated otherwise, such a diffraction phenomenon can be perceived and treated as a geometrical mapping problem. For example, in a measurement system in which uniqueness of mapping is preserved, combinations of the diffraction position and the diffraction angle are uniquely specified based on the X-ray detection results.

However, if attention is focused on the diffraction position (more specifically, the y coordinate) of the object to be measured M, uniqueness of mapping is not preserved in relation to the orthogonal direction A within the detection region R. Consequently, a phenomenon occurs in which the patterns 51 to 54 partially overlap, as shown in FIG. 3B. Although a discontinuous body (made up of discrete bodies) has been described above for ease of understanding, a similar phenomenon may occur even if a continuous body having a significant thickness is used.

Generally, in the case that measurement of an object to be measured M of this type is performed, a method of detecting only X-rays at a specific diffraction position (a specific y coordinate) using a confocal optical system is used. In this case, in order to carry out measurements at each of respective diffraction positions, it is necessary to sequentially repeat the operations of "relatively moving the object to be measured M" and "irradiating X-rays" onto the object to be measured M.

Stated otherwise, if the number of plots of the diffraction positions is large, a problem arises in that the time required for measurement becomes correspondingly longer. Similarly, such a problem also applies to measurements at each of respective diffraction angles. Thus, according to the present invention, an X-ray diffraction measurement method is proposed in which the object to be measured M can effectively be measured by a one-time X-ray detection operation.

[Operations of X-Ray Diffraction Measurement Apparatus 10]

Next, a description will be given with reference to the flowchart of FIG. 4 concerning operations of the X-ray diffraction measurement apparatus 10 according to the present embodiment.

Figure 4:
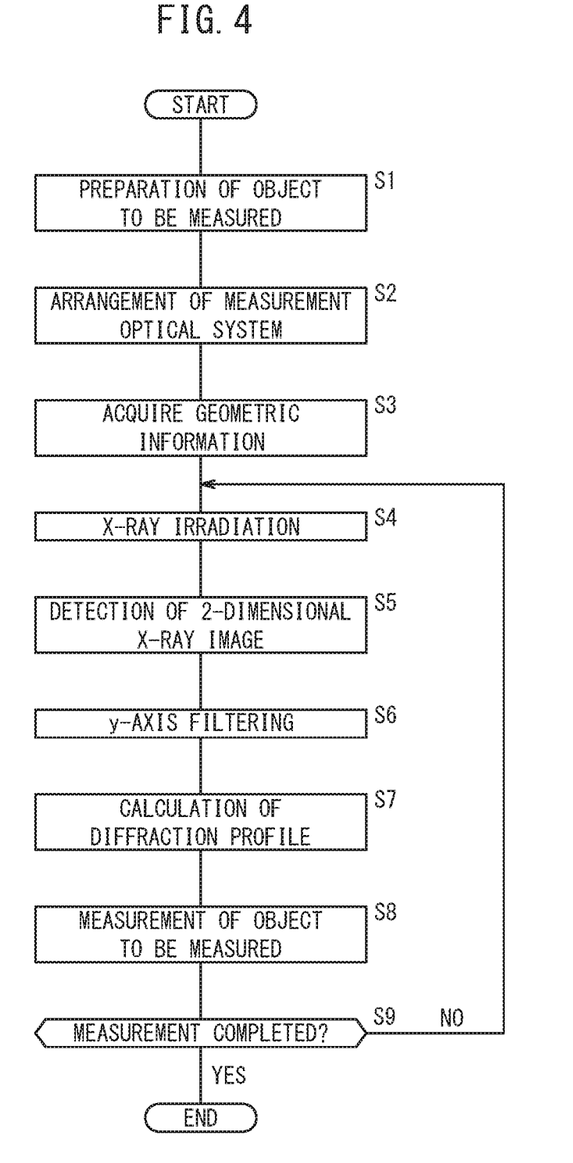
FIG. 4 is a flowchart for describing operations of the X-ray diffraction measurement apparatus shown in FIG. 1.

In step S1 of FIG. 4, an operator prepares the object to be measured M, and places the object to be measured M at a predetermined position (the intersecting position 34). The object to be measured M is an object that causes an X-ray diffraction phenomenon to be generated, and more specifically, is an object made from a polycrystalline material with orientational disorder, or alternatively, is an object including such a material.

For example, in the case that the object to be measured M is an object having a significant thickness (more specifically, greater than or equal to 10 µm), the object is placed at an orientation in which the thickness direction thereof lies parallel to the incident optical axis 30 (y-axis). Further, in the case that the object to be measured M is an object in which layered bodies 60a to 60c are stacked (see FIG. 3A), the object is placed at an orientation so that a stacking direction thereof lies parallel to the incident optical axis 30 (y-axis).

In step S2, the operator arranges (positionally adjusts) the measurement optical system in the X-ray diffraction measurement apparatus 10. In accordance therewith, the incident optical axis 30 and the outgoing optical axis 32 are adjusted so as to intersect with a predetermined angle of intersection 2θ at the intersecting position 34. It is noted that the material composition of the object to be measured M is already known to the operator, and therefore, the incident optical axis 30 and the outgoing optical axis 32 are set to an angle of intersection 2θ at which X-ray diffraction can easily be detected.

Moreover, the shielding plate 26 may be disposed so as to be capable of rotating with respect to the outgoing optical axis 32. In accordance with this feature, it is possible to change the direction of inclination B of the slit 24 to an orientation that is suitable for making measurements in accordance with the type of object to be measured M.

In step S3, the information acquisition unit 42 acquires geometric information in relation to the optical measurement system that was arranged in step S2. In this instance, the information acquisition unit 42 acquires geometric information for the purpose of specifying a positional relationship between the intersecting position 34, the slit 24, and the detection region R.

Figure 5A:
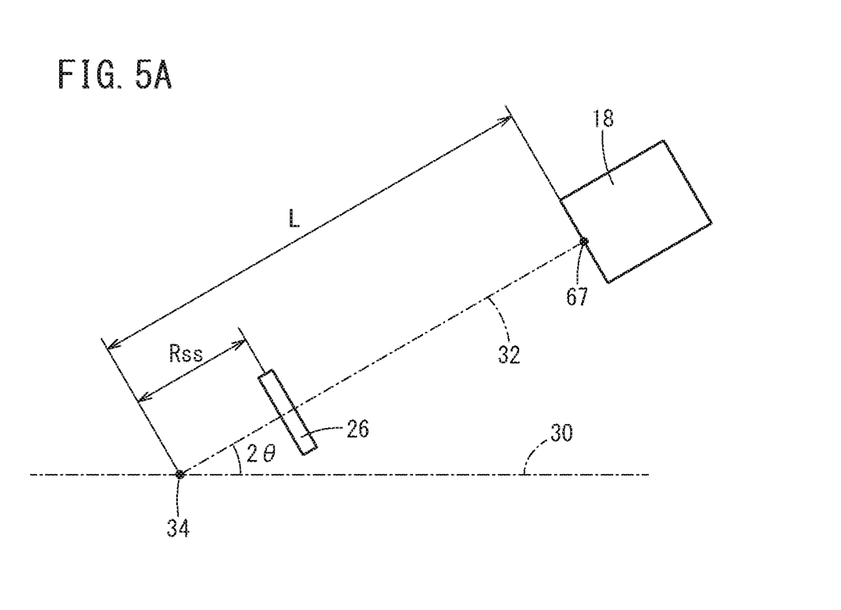
FIG. 5A is an explanatory diagram in relation to geometric information for specifying a relative positional relationship.

As shown in FIG. 5A, as geometric information for specifying the relative positional relationship, specifically, there is given, [1] the distance L from the intersecting position 34 to the two-dimensional detector 18, [2] the distance Rss from the intersecting position 34 to the shielding plate 26, [3] the angle of intersection 2θ formed between the incident optical axis 30 and the outgoing optical axis 32, [4] the coordinates (P, Q) corresponding to the position 67 on the outgoing optical axis 32, [5] the angle (in the illustrated example, an angle of zero degrees) formed between a line normal to the plane of the two-dimensional detector 18 and the outgoing optical axis 32, and [6] the angle (in the illustrated example, an angle of zero degrees) formed between a line normal to the shielding plate 26 and the outgoing optical axis 32.

Figure 5B:
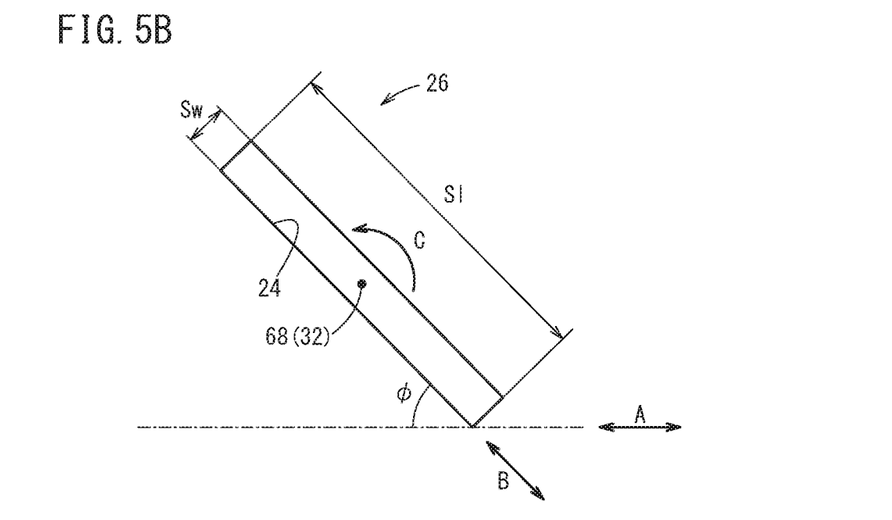
FIG. 5B is an explanatory diagram in relation to geometric information for specifying the shape of a slit.

As shown in FIG. 5B, as geometric information for specifying the shape of the slit 24, specifically, there is given [1] the angle of inclination φ (>0) of the slit 24, [2] the length S1 of the slit 24, [3] the width Sw of the slit 24, and [4] the amount of positional deviation between the slit center 68 and the outgoing optical axis 32 (in the illustrated example, the amount of positional deviation is zero).

In addition to geometric information, the information acquisition unit 42 may also acquire information concerning the shape or arrangement of the object to be measured M. As such information, specifically, there is given [1] the relative positioning of the object to be measured M and the intersecting position 34, and [2] the thickness (in the y-axis direction) of the object to be measured M.

In step S4, the X-ray generator 12 irradiates X-rays in accordance with a synchronous control performed by the synchronous control unit 40. Accordingly, the X-rays pass along the incident optical axis 30 through the pinhole 22 of the incident side shielding mechanism 14, and arrive at the measurement site 36 of the object to be measured M. After being diffracted at the diffraction position (a position in the interior or on the surface) of the object to be measured M, the X-rays pass along the outgoing optical axis 32 through the slit 24 of the shielding plate 26, and arrive at the two-dimensional detector 18.

In step S5, in accordance with the synchronous control performed by the synchronous control unit 40, the two-dimensional detector 18 detects the X-rays that have passed through the slit 24 in the detection region R, and outputs an obtained detection signal to the control device 20. Consequently, the control device 20 acquires the two-dimensional X-ray image 70 indicating the state of diffraction caused by the measurement site 36. The two-dimensional X-ray image 70 shown in FIG. 6A corresponds to an X-ray diffraction image produced by the object to be measured M of FIG. 3A.

Figure 6A:
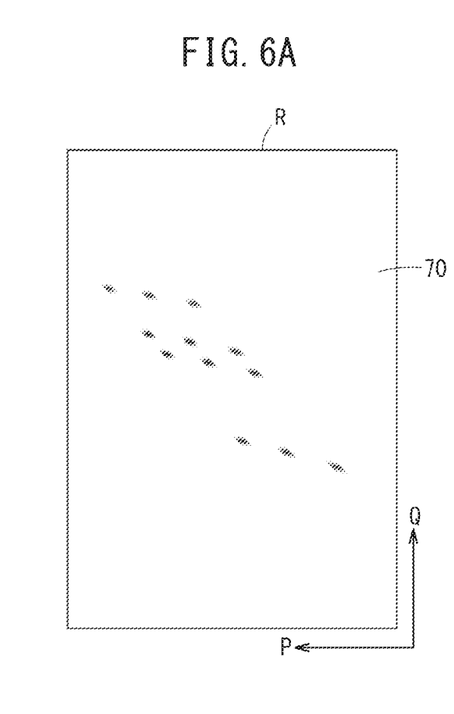
FIG. 6A is a diagram showing a two-dimensional X-ray image detected in a detecting step (step S5 of FIG. 4)
Figure 6B:
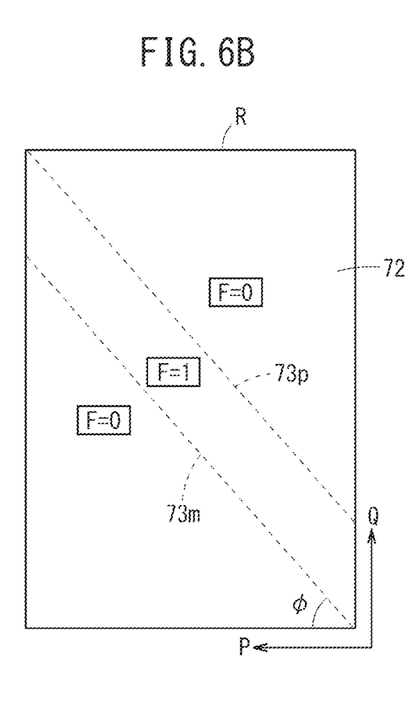
FIG. 6B is a diagram schematically showing a filter image used in a filtering step (step S6 of FIG. 4)

In step S6, the profile calculating unit 44 performs a filtering process with respect to the two-dimensional X-ray image 70 acquired in step S5, so as to limit the range of (the y coordinate of) the diffraction site. More specifically, the profile calculating unit 44 obtains a processed X-ray image 74 by applying a binary filter image 72 with respect to the two-dimensional X-ray image 70.

As shown in FIG. 6B, the filter image 72 includes an image region of the same shape as that of the two-dimensional X-ray image 70. Such an image region is partitioned into three sub-regions by two boundary lines 73p, 73m that are parallel to each other. Respective right triangular sub-regions with the boundary lines 73p, 73m serving as hypotenuses thereof indicate regions in which the filter coefficient F=0. The parallelogram-shaped sub-region which is surrounded by the boundary lines 73p, 73m indicates a region in which the filter coefficient F=1.

Incidentally, the respective boundary lines 73p, 73m are straight lines expressed by the following equation (1), using the coordinates (P, Q) of the two-dimensional position.

$$Q = P \cdot \tan\phi + \frac{L - R_{ss}}{R_{ss} - y_0 \cos 2\theta} y_0 \qquad (1)$$

The boundary line 73p is a straight line indicating a collection of detection positions of X-rays that pass through the upper edge of the slit 24, in the case that the diffraction angle is the angle of intersection 2θ, and the diffraction position is an upper limit value (y=yo). The boundary line 73m is a straight line indicating a collection of detection positions of X-rays and passing through the lower edge of the slit 24, in the case that the diffraction angle is the angle of intersection $2\theta$, and the diffraction position is a lower limit value (y=yo). In this instance, either one of the boundary lines 73p, 73m is inclined at the angle of inclination $\phi$ (>0) with respect to the P-axis direction (the orthogonal direction A).

For example, if the equation $\phi=0$ is satisfied (that is, if tan $\phi=0$), the first term on the right side of equation (1) becomes 0, and only the second term on the right side (a constant term independent of the value of P) remains. Stated otherwise, in the case that there are two or more combinations of (yo, $2\theta$) where the values of the second terms on the right side thereof are equal, the two-dimensional positions (P, Q) corresponding to such combinations all coincide.

On the other hand, as shown in FIG. 1, if the inequality $\phi>0$ is satisfied, the first term on the right side of equation (1) becomes non-zero, and therefore, Q assumes a value that depends on the value of P. It should be noted that, since the values of P corresponding to the combinations of (yo, $2\theta$) differ from each other, even if there are two or more combinations of (yo, $2\theta$) in which the constant terms thereof are equal, the two-dimensional positions (P, Q) differ from each other.

The profile calculating unit 44 multiplies the detection values (that is, the pixel values) of each pixel making up the two-dimensional X-ray image 70 by the binary filter coefficient F corresponding to the position of the pixel, and thereby carries out a filtering process on the diffraction positions. For example, in relation to the object to be measured M shown in FIG. 3A, in the case that the range of the diffraction positions (y coordinates) is set so as to include all of the layered bodies 60a to 60c, the processed X-ray image 74 shown in FIG. 6C is obtained.

Figure 6C:
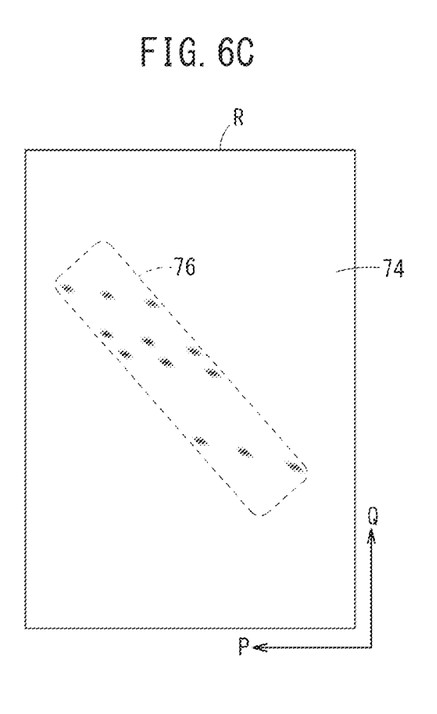
FIG. 6C is a view showing a result in which the filter image of FIG. 6B is applied with respect to the two-dimensional X-ray image of FIG. 6A.

As shown in FIG. 6C, the processed X-ray image 74 includes a dotted pattern group 76 composed of twelve individually identifiable dot-like patterns. The dotted pattern group 76 corresponds to a pattern group in which the patterns 51 to 54 (see FIG. 2) in the layered bodies 60a to 60c (see FIG. 3A) are cut out along the direction of inclination B of the slit 24.

In step S7, using the processed X-ray image 74 that was filtered in step S6, the profile calculating unit 44 calculates diffraction profiles for each of the diffraction positions. In this instance, the term "diffraction profile" implies a characteristic curve indicating the X-ray intensity with respect to the diffraction angle ($2\theta$obs) of the object to be measured M.

Figure 7A:
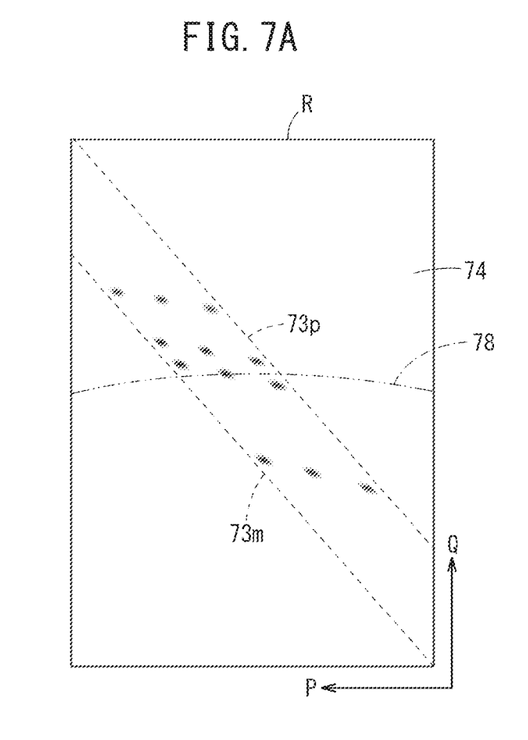
FIGS. 7A and 7B are explanatory diagrams in relation to a method of calculating a diffraction profile in a calculating step (step S7 of FIG. 4)

As shown in FIG. 7A, using the aforementioned geometric information, the profile calculating unit 44 calculates the projected positions of the diffracted X-rays corresponding to the specified values of (yo, $2\theta$obs), and more specifically, calculates a conic curve 78 corresponding to the projected positions of a Debye ring expressed in the form of an elliptical curve. In addition, the profile calculating unit 44 obtains the X-ray intensities at specified values of (yo, $2\theta$obs), by sequentially integrating the pixel values of all of the pixels lying on the conic curve 78.

Moreover, in the processed X-ray image 74, in accordance with the above-described filtering process, integration is valid only for pixels (non-zero pixel values) between the boundary lines 73p, 73m, whereas in relation to pixels apart therefrom (zero pixel values), integration thereof is rendered substantially invalid.

For example, the profile calculating unit 44 is capable of calculating diffraction profiles for each of the diffraction positions (y), by fixing the diffraction position y=yo, and then sequentially determining the X-ray intensities while changing the diffraction angle $2\theta$obs at an arbitrary step width.

Figure 7B:
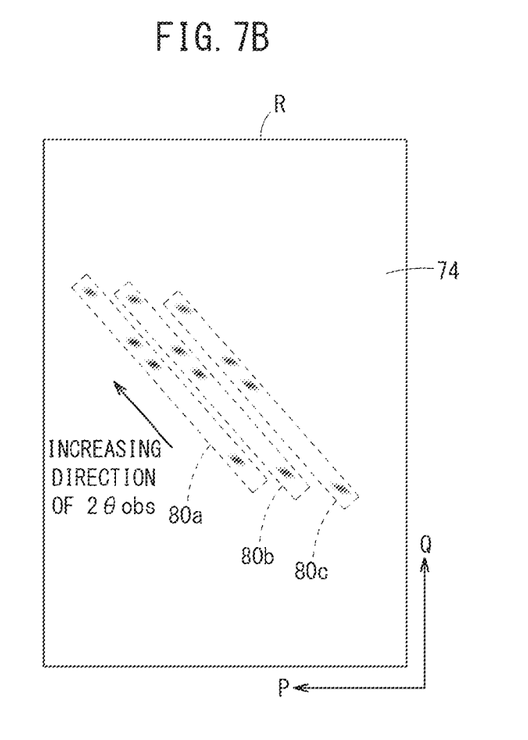

As shown in FIG. 7B, the one-dimensional X-ray images 80a to 80c are images corresponding to the positions of the layered bodies 60a to 60c, which are extracted from the two-dimensional X-ray image 70 along the direction of inclination B of the slit 24. The arrow shown in the drawing indicates an increasing direction of the diffraction angle $2\theta$obs. Moreover, the diffraction angle $2\theta$obs exhibits a non-linear correspondence relationship with respect to the position along the direction of inclination B.

Figure 8A:
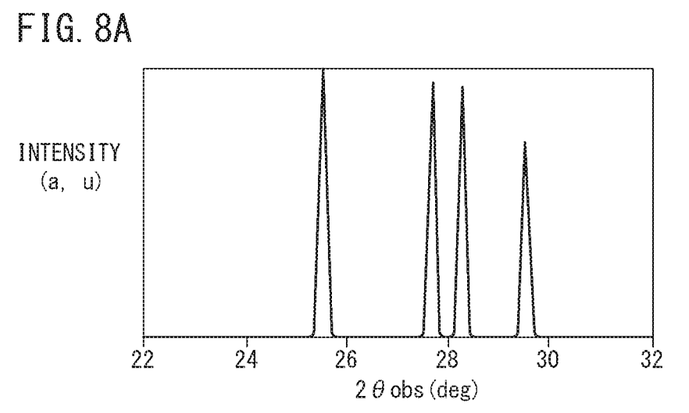
FIGS. 8A to 8C are diagrams showing diffraction profiles for each of respective positions of layered bodies.
Figure 8B:
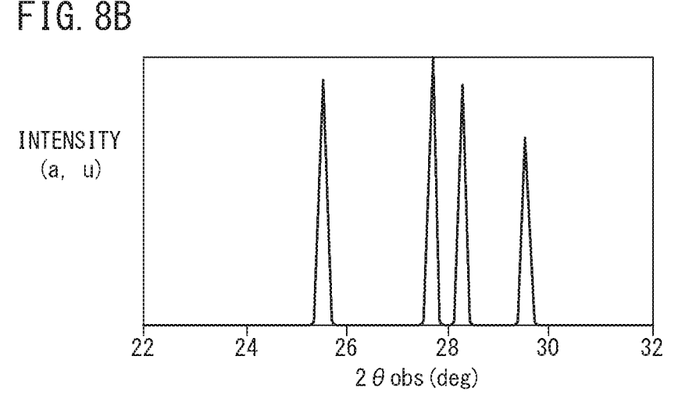
Figure 8C:
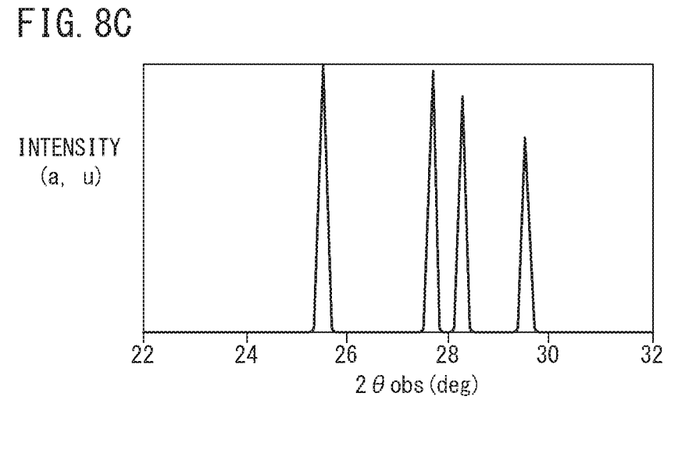

FIGS. 8A to 8C are diagrams showing diffraction profiles for each of the respective positions of the layered bodies 60a to 60c. Each of the graphs shows the X-ray intensity (units: arbitrary) with respect to the diffraction angle $2\theta$obs (units: degrees) of the object to be measured M. As can be understood from the drawings, diffraction profiles each having four peaks at the same diffraction angles $2\theta$obs are obtained, although the magnitude relationship of the peak intensities differ in each of the graphs.

The magnitude relationship of the peak intensities is believed to vary for the following reasons, namely, [1] because the area of the detection region R is of a finite size, and the detected length of the Debye rings differs depending on the diffraction angle $2\theta$obs, and [2] because there is a certain amount of crystal orientation in the material contained within the object to be measured M. In the case that it is desired to understand the relative magnitude relationship of the peak intensity in the same diffraction profile (as a specific example, in the case that information concerning the peak angles is extracted), there is no need to consider variations in the absolute values of the peak intensities.

In the foregoing manner, using the geometric information in relation to the intersecting position 34, the slit 24, and the detection region R, the profile calculating unit 44 calculates one or a plurality of diffraction profiles corresponding to the diffraction positions (y coordinates) of the object to be measured M. Since the slit 24 is a linear slit, diffraction profiles corresponding to respective diffraction positions can be calculated using a comparatively simple geometric calculation.

The object to be measured M may be a polycrystalline material with orientational disorder having a thickness of greater than or equal to 10 μm. By placing the object to be measured M in a suitable orientation, as was already described in step S2 of FIG. 4, properties at each of the respective positions in the thickness direction can be measured simultaneously by a one-time X-ray detection operation.

Alternatively, the object to be measured M may be an object in which the layered bodies 60a to 60c including a polycrystalline material with orientational disorder are stacked. By placing the object to be measured M in a suitable orientation, as was already described in step S2 of FIG. 4, properties at each of the respective layered bodies 60a to 60c can be measured simultaneously by a one-time X-ray detection operation.

In step S8, the property measurement unit 46 measures the properties of the measurement object M using the diffraction profile that was calculated in step S7. The properties may include, for example, a diffraction intensity, a lattice spacing, a lattice constant, a Miller index, the names of identified substances, concentration, stress, and temperature of the substances, and a charge/discharge depth of a battery active material.

In step S9, the control device 20 determines whether or not an indication of completion of measurement has been received. If a completion indication has not yet been received (step S9: NO), the process returns to step S4, and steps S4 to S9 are sequentially repeated. On the other hand, if an indication of completion of measurement has been received (step S9: YES), measurement of the object to be measured M is brought to an end.

In the case that the two-dimensional detector 18 is a photon counting type of detector, in a state in which the object to be measured M, the shielding plate 26, and the two-dimensional detector 18 are fixed, the profile calculating unit 44 is capable of calculating a time series of diffraction profiles on the basis of two-dimensional X-ray images 70 detected sequentially by the two-dimensional detector 18. In accordance with this feature, properties of the object to be measured M can be measured in time series, and a so-called dynamic analysis can be performed.

Advantages and Effects of the Present Embodiment

In the foregoing manner, the above-described X-ray diffraction measurement method [1] is a method for measuring properties of an object to be measured M by detecting an X-ray diffraction pattern produced by the object to be measured M at the intersecting position 34 where the incident optical axis 30 and the outgoing optical axis 32 intersect one another, comprising [2] an arranging step (step S2) of arranging on the outgoing optical axis 32 the shielding plate 26 having the linear slit 24 formed therein, and the two-dimensional detector 18 which is capable of detecting, within the detection region R, X-rays that have passed through the slit 24, and [3] a calculating step (step S7) of calculating a diffraction profile indicating an X-ray intensity with respect to a diffraction angle of the object to be measured M, on the basis of the two-dimensional X-ray image 70 detected by the two-dimensional detector 18, wherein, [4] in the arranging step, the shielding plate 26 is arranged in a manner so that the slit 24 is inclined at least in a direction C about the outgoing optical axis 32 with respect to an orthogonal direction A which is orthogonal to both the incident optical axis 30 and the outgoing optical axis 32.

Further, the above-described X-ray diffraction measurement apparatus 10 is [1] an apparatus adapted to measure properties of an object to be measured M by detecting an X-ray diffraction pattern produced by the object to be measured M at the intersecting position 34 where the incident optical axis 30 and the outgoing optical axis 32 intersect one another, comprising [2] the shielding plate 26 having the linear slit 24 formed therein, [3] the two-dimensional detector 18 which is capable of detecting, within the detection region R, X-rays that have passed through the slit 24, and [4] the profile calculating unit 44 adapted to calculate a diffraction profile indicating an X-ray intensity with respect to a diffraction angle of the object to be measured M, on the basis of the two-dimensional X-ray image 70 detected by the two-dimensional detector 18, wherein [5] the shielding plate 26 and the two-dimensional detector 18 are disposed respectively on the outgoing optical axis 32, and [6] the shielding plate 26 is arranged in a manner so that the slit 24 is inclined at least in a direction C about the outgoing optical axis 32 with respect to an orthogonal direction A which is orthogonal to both the incident optical axis 30 and the outgoing optical axis 32.

In the forgoing manner, by inclining the slit 24 at least in the direction C about the axis with respect to the orthogonal direction A, the passage of X-rays is limited in a manner so as to ensure uniqueness of the mapping. Stated otherwise, the diffraction position (yo) and the diffraction angle ($2\theta obs$) are uniquely determined from the two-dimensional position (P, Q) lying within the detection region R, and a diffraction profile corresponding to the diffraction position can be calculated on the basis of the detected two-dimensional X-ray image 70. Consequently, the object to be measured M can effectively be measured by a one-time X-ray detection operation.

Supplemental Considerations

The present invention is not limited to the above-described embodiment, and it goes without saying that the present invention can be freely modified within a scope that does not depart from the essence and gist of the present invention.

For example, in the example shown in FIG. 1, a shielding plate 26 having a slit 24 which extends in the direction of inclination B is used, however, the form of the arrangement is not limited to this feature. For example, a shielding plate 26 having a slit 24 which lies parallel with respect to one side of a rectangle may be arranged with the angle of inclination $\phi$ thereof inclined with respect to the horizontal plane (xy plane).

Further, in the example of FIG. 1, the two-dimensional detector 18 is fixed at a position that differs from that of the shielding plate 26, however, the form of the arrangement is not limited to this feature. For example, the two-dimensional detector 18 and the shielding plate 26 may be fixed integrally to an arm (not shown) in which the intersecting position 34 is the center of rotation thereof. By rotating the arm, it is possible to change the angle of intersection $2\theta$ while maintaining the relative position and attitude relationship between the two-dimensional detector 18 and the shielding plate 26.

What is claimed is:

1. An X-ray diffraction measurement method for measuring properties of an object to be measured by detecting an X-ray diffraction pattern produced by the object to be measured at an intersecting position where an incident optical axis and an outgoing optical axis intersect one another, comprising:

an arranging step of arranging on the outgoing optical axis
a shielding plate having a linear slit formed therein, and
a two-dimensional detector which is capable of detecting within a detection region X-rays that have passed through the slit; and a calculating step of calculating a diffraction profile indicating an X-ray intensity with respect to a diffraction angle of the object to be measured, on the basis of a two-dimensional X-ray image detected by the two-dimensional detector;

wherein, in the arranging step, the shielding plate is arranged in a manner so that the slit is inclined at least in a direction about the outgoing optical axis with respect to an orthogonal direction which is orthogonal to both the incident optical axis and the outgoing optical axis.

2. The X-ray diffraction measurement method according to claim 1, wherein, in the calculating step, one or a plurality of diffraction profiles corresponding to diffraction positions of the object to be measured are calculated using geometric information in relation to the intersecting position, the slit, and the detection region.

3. The X-ray diffraction measurement method according to claim 2, wherein the object to be measured is a polycrystalline material with orientational disorder, and is an object including a randomly oriented material having a thickness greater than or equal to 10 μm, and the object to be measured is arranged at an orientation so that the thickness direction of the object lies parallel to the incident optical axis.

4. The X-ray diffraction measurement method according to claim 2, wherein the object to be measured is an object in which layered bodies including a polycrystalline material with orientational disorder are stacked, and the object to be measured is arranged at an orientation so that a stacking direction of the layered bodies lies parallel to the incident optical axis.

5. The X-ray diffraction measurement method according to claim 1, wherein:
   the two-dimensional detector is a photon counting type of detector; and
   in the calculating step, in a state in which the object to be measured, the shielding plate, and the two-dimensional detector are fixed, a time series of diffraction profiles are calculated on the basis of two-dimensional X-ray images detected sequentially by the two-dimensional detector.

6. The X-ray diffraction measurement method according to claim 1, wherein the shielding plate is disposed so as to be capable of rotating with respect to the outgoing optical axis.

7. An X-ray diffraction measurement apparatus adapted to measure properties of an object to be measured by detecting an X-ray diffraction pattern produced by the object to be measured at an intersecting position where an incident optical axis and an outgoing optical axis intersect one another, comprising:
   a shielding plate having a linear slit formed therein;
   a two-dimensional detector which is capable of detecting within a detection region X-rays that have passed through the slit; and
   a profile calculating unit adapted to calculate a diffraction profile indicating an X-ray intensity with respect to a diffraction angle of the object to be measured, on the basis of a two-dimensional X-ray image detected by the two-dimensional detector;
   wherein the shielding plate and the two-dimensional detector are disposed respectively on the outgoing optical axis; and
   the shielding plate is arranged in a manner so that the slit is inclined at least in a direction about the outgoing optical axis with respect to an orthogonal direction which is orthogonal to both the incident optical axis and the outgoing optical axis.

\* \* \* \* \*